(12) United States Patent
Hishida

(10) Patent No.: US 8,758,680 B2
(45) Date of Patent: Jun. 24, 2014

(54) METHOD AND DEVICE FOR CLEANING AIR

(76) Inventor: Iwao Hishida, Toyonaka (JP)

(*) Notice: Subject to any disclaimer, the term of this patent is extended or adjusted under 35 U.S.C. 154(b) by 246 days.

(21) Appl. No.: 13/246,030

(22) Filed: Sep. 27, 2011

(65) Prior Publication Data

US 2012/0093683 A1 Apr. 19, 2012

(30) Foreign Application Priority Data

Sep. 29, 2010 (JP) ................. 2010-218598
Dec. 9, 2010 (JP) ................. 2010-274212

(51) Int. Cl.
| | | |
|---|---|---|
| *A61L 9/00* | (2006.01) | |
| *B01D 47/16* | (2006.01) | |
| *B01D 41/00* | (2006.01) | |
| *B01D 45/00* | (2006.01) | |
| *A01N 1/02* | (2006.01) | |
| *A61L 2/18* | (2006.01) | |
| *A61L 2/22* | (2006.01) | |
| *A61L 9/01* | (2006.01) | |
| *B01B 1/00* | (2006.01) | |
| *A61L 9/03* | (2006.01) | |
| *A61L 9/04* | (2006.01) | |
| *A61L 9/14* | (2006.01) | |

(52) U.S. Cl.
CPC .............. *A01N 1/0215* (2013.01); *A61L 2/18* (2013.01); *A61L 2/22* (2013.01); *A61L 9/00* (2013.01); *A61L 9/01* (2013.01); *B01B 1/005* (2013.01); *A61L 9/032* (2013.01); *A61L 9/04* (2013.01); *A61L 9/14* (2013.01); *A61L 9/145* (2013.01)
USPC ............ 422/5; 422/1; 422/4; 96/283; 96/284; 96/286; 95/218; 55/86; 55/90; 55/247; 261/91

(58) Field of Classification Search
CPC .......... A01N 1/0215; A61L 2/18; A61L 2/22; A61L 9/00; A61L 9/01; A61L 9/032; A61L 9/04; A61L 9/14; A61L 9/145; B01B 1/005
USPC ........ 422/1, 4–5, 292, 300, 900; 96/283–284, 96/286; 95/218; 55/86, 90–92, 247; 261/91
See application file for complete search history.

(56) References Cited

U.S. PATENT DOCUMENTS

2006/0096461 A1* 5/2006 Kim et al. ............... 96/283

FOREIGN PATENT DOCUMENTS

| JP | 7-17324 U | 3/1995 |
| JP | 2007-229047 A | 9/2007 |
| JP | 2008-520424 A | 6/2008 |
| WO | WO 2006/054856 A1 | 5/2006 |

* cited by examiner

*Primary Examiner* — Jill Warden
(74) *Attorney, Agent, or Firm* — Kratz, Quintos & Hanson, LLP

(57) ABSTRACT

The present invention is to provide an air cleaning method and device that realize sufficient purification of polluted air, high-efficiency removal of germs or the like from polluted air, and has a relatively simplified structure.

10 Claims, 6 Drawing Sheets

METHOD AND DEVICE FOR CLEANING AIR

TECHNICAL FIELD

Figure 1:
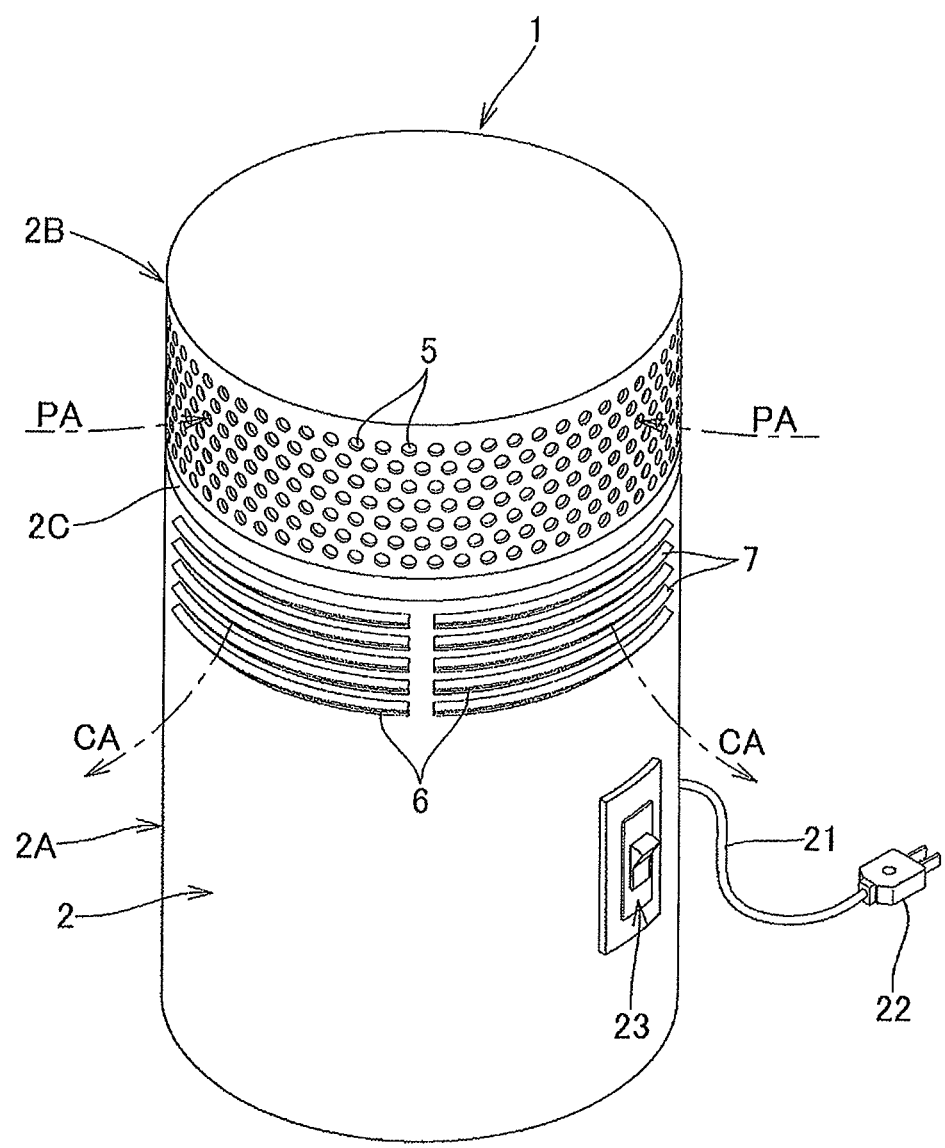
Figure 2:
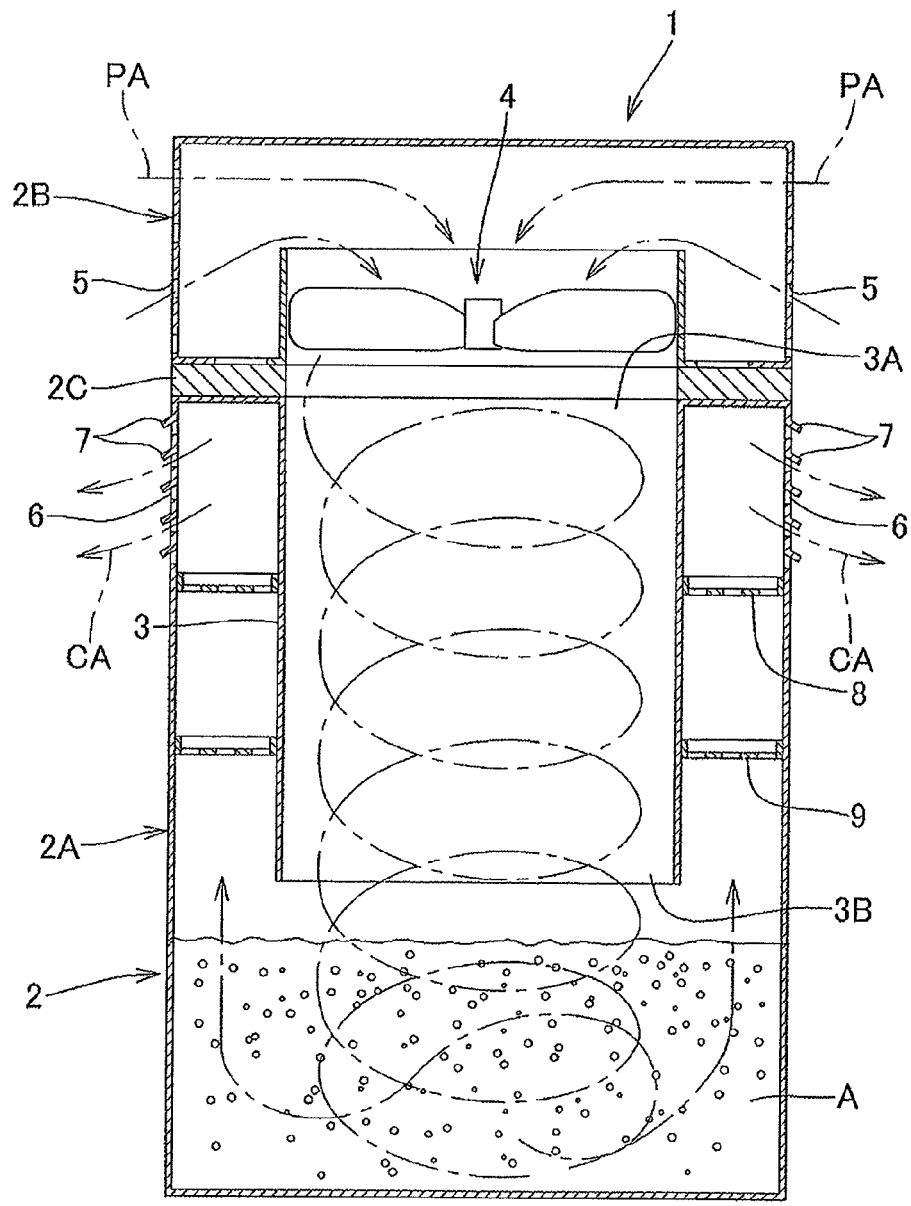

The present invention relates to methods and devices for cleaning air to purify indoor air polluted by dust, germs, and the like.

BACKGROUND ART

At present, indoor air in houses, hospitals, buildings, and the like, has been increasingly polluted. Pollutants include dust, molds, ticks, pollens, and various pathogenic germs including influenza viruses, tuberculosis bacteria, methicillin-resistant *Staphylococcus aureus* (MRSA) as nosocomial infectious bacteria, *Legionella* bacteria, coronaviruses such as severe acute respiratory syndrome (SARS) viruses, noroviruses, campylobacter, O-157 as food-poisoning germs, and the like. These various kinds of pollutants including floating fungus and airborne infectious germs are suspended in indoor space or attached to indoor wall surfaces, ceilings, furniture, and the like, to thereby deteriorate indoor environments and exert enormous harmful effects on human bodies.

There is suggested an air cleaning device for purifying indoor air polluted by the foregoing pollutants (hereinafter, referred to as "polluted air") that includes: a wind tunnel with an air inlet and an air outlet vertically arranged; a fan which takes polluted air into the wind tunnel from the air inlet and discharges the same from the air outlet; a nozzle which scatters liquid pressurized by a pump to an entire air path of the wind tunnel; and a collection tank for collecting the liquid, in which the polluted air taken by the fan into the wind tunnel contacts the liquid scattered from the nozzle, whereby the polluted air is purified (for example, refer to Patent Document 1).

In addition, there is suggested another air cleaning device in which pumped-up water is reflected on a mushroom-shaped reflector and turned into a spray of water, and polluted air taken in by an intake fan from an upper entry of a housing contacts the spray of water spreading over the housing, whereby the polluted air is purified (for example, refer to Patent Document 2).

Further, there is suggested another air cleaning device that includes: a housing retaining cleaning water; an air blower which is arranged above the cleaning water to blow polluted air downward from a fan; and a guide which extends from an lower end of the air blower into the cleaning water, increases in diameter downward, has a rib as a spiral projection therein, and is fixed to a rotation shaft of the air blower so as to rotate together with the fan, in which the polluted air blown downward by the fan contacts the cleaning water transferred upward by the rotation of the guide, whereby the polluted air is purified (for example, refer to Patent Document 3).

CITATION LIST

Patent Literature

Patent Document 1: JP-A No. 7-17324
Patent Document 2: EP Application Public-disclosure No. 1506805 specification
Patent Document 3: JP-A No. 2008-520424

SUMMARY OF INVENTION

Technical Problem

The air cleaning device described in Patent Document 1 requires a pump and a nozzle, which leads to increase of manufacturing costs. In addition, the air cleaning device of Patent Document 1 is configured to let polluted air contact the surface of water drops scattered from a nozzle, but the time of contact between the liquid and the polluted air is comparatively short. This results in insufficient purification of the polluted air which may reduce the efficiency of removing germs and the like.

The air cleaning device described in Patent Document 2 requires a pump and a reflector, which leads to increase of manufacturing costs. In addition, the air cleaning device of Patent Document 2 is configured to let polluted air contact the surface of water mist spreading into a housing, but the time of contact between the liquid and the polluted air is comparatively short. This results in insufficient purification of the polluted air which may reduce the efficiency of removing germs and the like.

The air cleaning device described in Patent Document 3 is configured to have a guide extended from the lower end of an air blower into cleaning water and fixed to a rotation shaft of the air blower so as to rotate together with the rotation shaft. This requires a large-capacity motor for rotating the air blower fan and the guide, and complicates a support structure of the rotation shaft, which leads to increase in consumption of energy such as electric power and manufacturing costs.

In addition, even if the air cleaning device of Patent Document 3 is configured in such a manner that the guide extended into the cleaning water and increased in diameter downward does not rotate but the air blower fan rotates alone, the lower opening of the guide for blowing the polluted air is positioned in the cleaning water, which requires a large capacity air blower due to a high resistance of the cleaning water. This also brings about increase in consumption of energy such as electric power and manufacturing costs.

In light of the foregoing circumstances, an object of the present invention is to provide an air cleaning method and device that realize sufficient purification of polluted air, high-efficiency removal of germs and the like from polluted air, a relatively simplified structure, and suppression of increase in manufacturing costs.

Solution to Problem

To solve the foregoing issue, an air cleaning method of the present invention includes: pressurizing by an air blower air taken into a container main body containing a liquid as sterilizing fluid, deodorant fluid, or water; blowing the air pressurized by the air blower into a cylindrical body which has upper and lower openings and extends in a vertical direction, from the upper opening, the lower opening being an air blowing port separated from a surface of the liquid; blowing out of the lower opening, the air blown from the upper opening into the cylindrical body and rotating and descending in a spiral manner, so as to collide with the liquid, plunging the air into a bottom of a liquid containing part for containing the liquid in the container main body, and agitating and mixing the air and the liquid; and raising the air agitated and mixed with the liquid on an outside of the cylindrical body, and discharging the same to an outside of the container main body.

According to this configuration, the air taken into the container main body is pressurized by the air blower, and rotates and descends in a spiral manner by rotation of blades of the air blower and contact with the inner wall surface of the cylindrical body, and is blown out of the lower opening as an air blowing port toward the liquid surface, and collides with the liquid and plunges into the bottom of the liquid containing part (container bottom), and is agitated and mixed with an approximately total amount of the liquid as if the air is washed by the liquid. Therefore, the air taken into the container main body is allowed to contact the liquid with efficiency.

Accordingly, it is possible to remove pollutants such as dust, dirt, molds, ticks, pollens, and the like, in an efficient manner. In addition, if the liquid is sterilizing fluid, it is also possible to kill and remove pollutants such as viruses, germs, and the like, in an efficient manner. If the liquid is deodorant fluid, it is possible to eliminate bad odors of cigarette, formalin, and the like, in an efficient manner. If the liquid is water, it is possible to remove dust from construction sites, plants, and the like, in an efficient manner.

In addition, the thus configured air cleaning device does not require a pump or a nozzle as described in Patent Document 1 or a pump or a reflector as described in Patent Document 2. Further, this air cleaning device is not configured to rotate a guide fixed to the rotation shaft of the air blower and extended into the cleaning water as in Patent Document 3, and therefore the cylindrical body positioned under the air blower is not driven and the lower opening of the cylindrical body as an air blowing port is separated from the surface of the liquid. This does not require a large-capacity air blower or motor or a complicated structure, which makes it possible to suppress increase in consumption of energy such as electric power and manufacturing costs.

To solve the foregoing issue, an air cleaning method of the present invention includes: pressurizing by an air blower air taken into a container main body containing a liquid as sterilizing fluid, deodorant fluid, or water; blowing the air pressurized by the air blower into a cylindrical body which has upper and lower openings and extends in a vertical direction, from the upper opening, the lower opening being an air blowing port separated from a surface of the liquid; pumping up and pressurizing the liquid, and ejecting the liquid upward from the nozzle so as to collide with a reflector separated inward from the cylindrical body; contacting the air blown from the upper opening into the cylindrical body and rotating and descending in a spiral manner with the liquid colliding with and scattered by the reflector; causing a mixture of the air falling from the cylindrical body and the scattered liquid to collide with a puddle of liquid in the container main body, plunging the mixture into a bottom of a liquid containing part for containing the liquid in the container main body, and agitating and mixing the air with the liquid; and raising the air agitated and mixed with the liquid on an outside of the cylindrical body and discharging the same to an outside of the container main body.

According to this configuration, the air taken into the container main body is pressurized by the air blower, and rotates and descends in a spiral manner by rotation of the blades of the air blower and contact with the inner wall surface of the cylindrical body, and the liquid as a jet flow ejected from the nozzle is scattered by collision with the reflector separated inward from the cylindrical body, and the air rotating and descending in a spiral manner and the liquid colliding with and scattered by the reflector are brought into contact within the cylindrical body, and a mixture of the air and the liquid sharply falls in a bubble state.

The bubbled mixture collides with the liquid contained in the lower part of the container, and penetrates through the puddle of liquid and plunges into the bottom of the liquid containing part (container bottom). Accordingly, the entire liquid puddle is also strongly agitated and mixed in a spiral manner so as to bubble, swell, and increase in volume, as if the air is washed by the liquid. Therefore, the air taken into the container main body is allowed to contact the liquid with extremely high efficiency.

Accordingly, it is possible to remove pollutants such as dust, dirt, molds, ticks, pollens, and the like, in a highly efficient manner. In addition, if the liquid is sterilizing fluid, it is also possible to kill and remove pollutants such as viruses, germs, and the like, in a highly efficient manner. If the liquid is deodorant fluid, it is possible to eliminate bad odors of cigarette, formalin, and the like, in a highly efficient manner. If the liquid is water, it is possible to remove dust from construction sites, plants, and the like, in a highly efficient manner.

Besides, if the air taken in from the air inlet is hot wind, for example, the hot wind can be cooled down by airborne droplets of the liquid colliding with and reflected on the reflector and scattered in various directions. In addition, since the liquid as a jet flow collides from below with the reflector heated by transfer of forced convection heat from the hot wind, the hot wind can be cooled down via the reflector by high-efficiency colliding jet cooling. Accordingly, in any of cases where the liquid is sterilizing fluid or deodorant fluid or water, this configuration is suited for cooling hot air in working sites or the like at high temperatures.

Moreover, differently from the configuration described in Patent Document 3 with rotation of the guide fixed to the rotation shaft of the air blower and extended in the cleaning water, in this configuration, the cylindrical body arranged under the air blower is not driven and the lower opening of the cylindrical body as an air blowing port is separated from the surface of the liquid, which eliminates the need for a large-capacity air blower or motor and prevents a structure from being complicated. This makes it possible to suppress increase in consumption of energy such as electrical power and manufacturing costs.

In this arrangement, it is preferred to raise the air agitated and mixed with the liquid on the outside of the cylindrical body and remove the liquid from the air in the middle of a flow path for discharging the air to the outside of the container main body.

According to this configuration, the air agitated and mixed with the liquid is raised and cleared of the liquid before being discharged to the outside of the container main body. This makes it possible to suppress a content of the liquid in the discharged air and reduce decrease in amount of the liquid in the container main body, thereby to realize longer time intervals between tasks of refilling the liquid.

To solve the foregoing issue, an air cleaning device in the present invention includes: a container main body which contains a liquid as sterilizing fluid, deodorant fluid, or water; a cylindrical body which has upper and lower openings and extends in a vertical direction, which is arranged within the container main body such that the lower opening is separated from a surface of the liquid; an air blower which is arranged above the cylindrical body within the container main body, and pressurizes the air taken in from the air inlet of the container main body, and blows the same from the upper opening as an air blowing port into the cylindrical body; and an air outlet which is formed on an outside of the cylindrical body of the container main body, wherein the air blown by the air blower from the upper opening into the cylindrical body, rotates and descends in a spiral manner and is blown out from the lower opening as an air blowing port, and collides with the liquid and plunges into a bottom of a liquid containing part for containing the liquid in the container main body, and is agitated and mixed with the liquid, and the air agitated and mixed with the liquid is raised on the outside of the cylindrical body and is discharged from the air outlet.

According to this configuration, the air taken in from the air inlet is pressurized by the air blower, and rotates and descends in a spiral manner by rotation of blades of the air blower and contact with the inner wall surface of the cylindrical body, and is blown out of the lower opening as an air blowing port toward the liquid surface, and collides with the liquid and plunges into the bottom of the liquid containing part (container bottom), and is agitated and mixed with an approximately total amount of the liquid as if the air is washed by the liquid. Therefore, the air taken in from the air inlet is allowed to contact the liquid with efficiency.

Accordingly, it is possible to remove pollutants such as dust, dirt, molds, ticks, pollens, and the like, in an efficient manner. In addition, if the liquid is sterilizing fluid, it is also possible to kill and remove pollutants such as viruses, germs, and the like, in an efficient manner. If the liquid is deodorant fluid, it is possible to eliminate bad odors of cigarette, formalin, and the like, in an efficient manner. If the liquid is water, it is possible to remove dust from construction sites, plants, and the like, in an efficient manner.

In addition, the thus configured air cleaning device does not require a pump or a nozzle as described in Patent Document 1 or a pump or a reflector as described in Patent Document 2. Further, this air cleaning device is not configured to rotate a guide fixed to the rotation shaft of the air blower and extended into the cleaning water as in Patent Document 3, and therefore the cylindrical body positioned under the air blower is not driven and the lower opening of the cylindrical body as an air blowing port is separated from the surface of the liquid. This does not require a large-capacity air blower or motor or a complicated structure, which makes it possible to suppress increase in consumption of energy such as electric power and manufacturing costs.

In this arrangement, a bar-like body is preferably provided so as to stand on the bottom of the liquid containing part and extend toward an approximate center of the cylindrical body.

According to this configuration, the bar-like body brings about a smaller passage section of the air blown out of the cylindrical body and colliding with the liquid. This increases a pressure of the air rotating and descending in a spiral manner, thereby to facilitate the agitation and mixture of the air and the liquid.

Therefore, the air taken in from the air inlet can contact the liquid with higher efficiency.

In addition, baffles are preferably provided so as to project from the bottom or side of the liquid containing part.

According to this configuration, the agitation and mixture of the air spirally rotating and descending and the liquid can be facilitated by the agitation facilitating effect of the baffles. This allows the air taken in from the air inlet to contact the liquid with higher efficiency.

Further, an agitator is preferably arranged on the bottom of the liquid containing part.

According to this configuration, the agitation and mixture of the air spirally rotating and descending and the liquid can be facilitated by the agitation facilitating effect of the agitator. This allows the air taken in from the air inlet to contact the liquid with higher efficiency.

To solve the foregoing issue, an air cleaning device in the present invention includes: a container main body which contains a liquid as sterilizing fluid, deodorant fluid, or water; a cylindrical body which has upper and lower openings and extends in a vertical direction, which is arranged within the container main body such that the lower opening is separated from a surface of the liquid; an air blower which is arranged above the cylindrical body within the container main body, and pressurizes the air taken in from the air inlet of the container main body, and blows the same from the upper opening as an air blowing port into the cylindrical body; a pump which pumps up and pressurizes the liquid; a nozzle which is upwardly attached to a discharging port of the pump; a reflector which is provided above the nozzle, and is separated inward from the cylindrical body, and collides with the liquid as a jet flow ejected from the nozzle and reflects the same; and an air outlet which is formed on an outside of the cylindrical body of the container main body, wherein the air blown by the air blower from the upper opening into the cylindrical body, rotates and descends in a spiral manner, and contacts the liquid colliding with and scattered by the reflector, and a mixture of the air falling from the lower opening as an air blowing port and the scattered liquid collides with a puddle of liquid in the container main body and plunges into a bottom of a liquid containing part for containing the liquid in the container main body, and is agitated and mixed with the liquid, and the air agitated and mixed with the liquid is raised on the outside of the cylindrical body and discharged from the air outlet.

According to this configuration, the air taken into the container main body is pressurized by the air blower, and rotates and descends in a spiral manner by rotation of the blades of the air blower and contact with the inner wall surface of the cylindrical body, and the liquid as a jet flow ejected from the nozzle is scattered by collision with the reflector separated inward from the cylindrical body, and the air rotating and descending in a spiral manner and the liquid colliding with and scattered by the reflector are brought into contact within the cylindrical body, and a mixture of the air and the liquid sharply falls in a bubble state.

The bubbled mixture collides with the liquid contained in the lower part of the container, and penetrates through the puddle of liquid and plunges into the bottom of the liquid containing part (container bottom). Accordingly, the entire liquid puddle is also strongly agitated and mixed in a spiral manner so as to bubble, swell, and increase in volume, as if the air is washed by the liquid. Therefore, the air taken into the container main body is allowed to contact the liquid with extremely high efficiency.

Accordingly, it is possible to remove pollutants such as dust, dirt, molds, ticks, pollens, and the like, in a highly efficient manner. In addition, if the liquid is sterilizing fluid, it is also possible to kill and remove pollutants such as viruses, germs, and the like, in a highly efficient manner. If the liquid is deodorant fluid, it is possible to eliminate bad odors of cigarette, formalin, and the like, in a highly efficient manner. If the liquid is water, it is possible to remove dust from construction sites, plants, and the like, in a highly efficient manner.

Besides, if the air taken in from the air inlet is hot wind, for example, the hot wind can be cooled down by airborne droplets of the liquid colliding with and reflected on the reflector and scattered in various directions. In addition, since the liquid as a jet flow collides from below with the reflector heated by transfer of forced convection heat from the hot wind, the hot wind can be cooled down via the reflector by high-efficiency colliding jet cooling. Accordingly, in any of cases where the liquid is sterilizing fluid or deodorant fluid or water, this configuration is suited for cooling hot air in working sites or the like at high temperatures.

Moreover, differently from the configuration described in Patent Document 3 with rotation of the guide fixed to the rotation shaft of the air blower and extended in the cleaning water, in this configuration, the cylindrical body arranged under the air blower is not driven and the lower opening of the cylindrical body as an air blowing port is separated from the surface of the liquid, which eliminates the need for a large-capacity air blower or motor and prevents a structure from being complicated. This makes it possible to suppress increase in consumption of energy such as electrical power and manufacturing costs.

In this arrangement, a guide body is preferably provided within the cylindrical body under the reflector so as to receive the liquid colliding with and reflecting on the reflector, and guide the same outward.

According this configuration, a part of the liquid scattered by collision with the upper guide body, further collides with the lower guide body, and is guided outward and scatters by the lower guide body. Accordingly, airborne droplets of the scattered liquid are guided into a mixing space inside the cylindrical body. This increases the density of airborne droplets of the liquid within the mixing space, which allows the air taken in from the outside to contact the liquid with higher efficiency.

Further, a liquid removing means is preferably provided in the middle of a flow path for raising the air agitated and mixed with the liquid on the outside of the cylindrical body and discharging the same from the air outlet.

According to this configuration, the air agitated and mixed with the liquid is raised and cleared of the liquid by a liquid removing means before being discharged to the outside of the container main body. This makes it possible to suppress a content of the liquid in the discharged air and reduce decrease in amount of the liquid in the container main body, thereby to realize longer time intervals between tasks of refilling the liquid.

Advantageous Effects of Invention

As in the foregoing, according to the air cleaning method and device in the present invention, the air taken into the container main body and pressurized by the air blower, is blown from the upper opening into the cylindrical body with the lower opening (blowing port) separated from the surface of the liquid, so as to rotate and descend in a spiral manner, and the air is strongly blown out of the lower opening as a blowing port toward the liquid surface, or a mixture formed by contacting the air spirally rotating and descending within the cylindrical body with the liquid colliding with and scattered by the reflector, is strongly blown out of the lower opening toward the liquid surface, such that the mixture collides with the liquid puddle and plunges into the bottom of the liquid containing part, whereby the air taken into the container main body is agitated and mixed with the liquid. This allows the air to contact the liquid with efficiency, thereby achieving sufficient purification of the polluted air. Accordingly, these method and device provide significant advantages of removing efficiently germs and the like from the polluted air, simplifying the structure, and suppressing increase of manufacturing costs.

BRIEF DESCRIPTION OF THE DRAWINGS

FIG. 1 is a perspective view of an air cleaning device in an embodiment of the present invention;

FIG. 2 is a partial longitudinal sectional view of the same;

FIG. 3 is a partial longitudinal sectional view of a configuration in which a bar-like body is provided so as to stand on a bottom of a liquid containing part of a container main body;

FIG. 4 is a partial longitudinal sectional view of a configuration in which baffles are provided so as to project from the bottom of the liquid containing part of the container main body;

FIG. 5 is a partial longitudinal sectional view of a configuration in which an agitator is arranged on the bottom of the liquid containing part of the container main body; and FIG. 6 is a partial longitudinal sectional view of a configuration in which air spirally rotating and descending within a cylindrical body and liquid scattered by collision with a reflector, are contacted and mixed together.

DESCRIPTION OF EMBODIMENTS

The perspective view in FIG. 1 shows an embodiment with an air cleaning device 1 for indoor use, for example, domestic use, which is brought into an operational state by inserting a power plug 22 at a leading end of a power cord 21 into a socket not shown and then turning on a switch 23.

When the air cleaning device 1 is in the operational state, polluted air PA is taken in from air inlets 5, 5, . . . formed at an upper part of a side surface of a container main body 2. The polluted air PA contacts sterilizing fluid, deodorant fluid, or water, contained in the container main body 2, and then is discharged as clean air CA with no unpleasant odor, from air outlets 6, 6, . . . .

In this arrangement, since downwardly-inclined louvers 7, 7, . . . are provided at upper edge portions of the air outlets 6, 6, . . . , the clean air CA is discharged downward from the air outlets 6, 6, . . . , thereby to suppress suction of the clean air CA from the air inlets 5, 5, . . . .

As shown in the partial longitudinal sectional view of FIG. 2, the air cleaning device 1 in the embodiment of the present invention includes: the container main body 2 that contains liquid A as sterilizer, deodorizer, or water in a liquid container 2A; a cylindrical body 3 with upper and lower openings 3A and 3B that is arranged within the container main body 2 and extends in a vertical direction such that the lower opening 3B is separated from a surface of the liquid A; an air blower 4 that is arranged above the cylindrical body 3 within the container main body 2, pressurizes the polluted air PA taken in from the air inlets 5, 5, . . . of the container main body 2, and blows the same into the cylindrical body 3 from the upper opening 3A as an air blowing port; and the air outlets 6, 6, . . . formed on an outside of the cylindrical body 3 of the container main body 2.

As shown in FIGS. 1 and 2, the container main body 2 of the air cleaning device 1 is an approximately circular cylinder in appearance, and is configured in such a manner that a liquid container 2A which serves as a liquid containing part for containing the liquid A and has the louvers 7, 7, . . . on a side surface of an upper part thereof and the air outlets 6, 6, . . . as long holes extending in a circumferential direction under these louvers 7, 7, . . . , is connected by a connecting member 2C to an air blower assembly 2B which has the air inlets 5, 5, . . . as a large number of round holes on the side surface thereof.

In addition, the cylindrical body 3 extending in a vertical direction and having the upper and lower openings 3A and 3B, is arranged above the liquid A and under the air blower 4 within the container main body 2, such that the lower opening 3B as an air blowing port is separated from the liquid A. Arranged on an outside of the cylindrical body 3 are upper and lower metal draining meshes 8 and 9 as liquid removing means.

The liquid removing means may not be metal draining meshes but may be filters, impellers, cyclone centrifugal separators, or the like.

The polluted air PA taken in from the air inlets 5, 5, . . . is pressurized by the air blower 4 and blown from the upper opening 3A into the cylindrical body 3. The polluted air PA then rotates and descends in a spiral manner by rotation of blades of the air blower 4 and contact with an inner wall surface of the cylindrical body 3, and is blown out of the lower opening 3B as an air blowing port toward the liquid surface so as to collide with the liquid A, and plunges into a container bottom (a bottom of the liquid container 2A), and then is agitated and mixed with the liquid A. The clean air CA having been agitated and mixed with the liquid A is raised on the outside of the cylindrical body 3, and then is discharged from the air outlets 6, 6, . . . .

Arranging a whorl-like grill or the like under the blades of the air blower 4 can provide a stronger spiral rotating force.

In this arrangement, the degree of agitation and mixture of the polluted air PA and the liquid A depends on specification data such as air volume and air pressure at the air blower 4, shape and length in a vertical direction of the cylindrical body 3, and amount (depth) of the liquid A. For example, if the cylindrical body 3 is too short in a vertical direction, the polluted air PA does not descend in a spiral manner or descends in a weaken spiral manner, and if the cylindrical body 3 is too long in a vertical direction, larger friction loss is generated to lower the air pressure. In either case, there is a tendency that the polluted air PA and the liquid A are agitated and mixed to a lowered degree.

Therefore, according to the specifications of air purifying performance and the like required for the air cleaning device 1, the foregoing specification data is determined by experiment or simulation or the like, such that the polluted air PA pressurized by the air blower 4 and blown into the cylindrical body 3 rotates and descends in a spiral manner so as to collide with the liquid A, and plunges into the container bottom, and then is agitated and mixed to a desired degree.

For reference, Tables 1 to 3 show results of testing at which mixing states of the air and the liquid are observed with a distance set at 20 mm between the lower opening 3B as an air blowing port and the surface of the liquid A, using an AC fan produced by Sanyo Denki Co., Ltd. (model no. 109S075UL) as the air blower 4.

It can be understood from the test results in Table 1 with variations in shape of the cylindrical body 3, that a circular cylindrical body with the upper and lower openings 3A and 3B identical in diameter produces a more favorable mixing state than a cylindrical body with the upper and lower openings 3A and 3B decreased or increased in diameter downward. It can be understood from the test results in Table 2 with variations in length of the cylindrical body 3, that the mixing state becomes more weakened with increase of length in the cylindrical body 3. It can be understood from the test results in Table 3 with variations in liquid amount and liquid depth, that the mixing state becomes more weakened with increase of liquid amount and liquid depth.

TABLE 1

| | | | |
|---|---|---|---|
| Diameter of upper opening 3A | 115 mm | 115 mm | 115 mm |
| Diameter of lower opening 3B | 115 mm | 90 mm | 130 mm |
| Length of cylindrical body 3 | 230 mm | 230 mm | 230 mm |
| Distance between lower opening 3B and liquid surface | 20 mm | 20 mm | 20 mm |
| Mixing state | Liquid rotates favorably in agitation and mixing. Mixing state is favorable. | Decreased amount of air is blown into liquid. Mixing state is slightly insufficient. | Preferred amount of air is blown into liquid, but pressure of air blown into liquid is low. Mixing state is slightly insufficient. |

TABLE 2

| | | | |
|---|---|---|---|
| Diameter of upper opening 3A | 115 mm | 115 min | 115 mm |
| Diameter of lower opening 3B | 115 mm | 115 mm | 115 mm |
| Length of cylindrical body 3 | 115 mm | 230 mm | 345 mm |
| Distance between lower opening 3B and liquid surface | 20 mm | 20 mm | 20 mm |
| Mixing state | Liquid swells vigorously in agitating and mixing. Mixing state is extremely favorable. | Liquid rotates favorably in agitation and mixing. Mixing state is favorable. | Pressure of air blown into liquid is low, and agitation and mixing are weakened. Mixing state is slightly insufficient. |

TABLE 3

| | | | |
|---|---|---|---|
| Diameter of upper opening 3A | 115 mm | 115 mm | 115 mm |
| Diameter of lower opening 3B | 115 mm | 115 mm | 115 mm |
| Length of cylindrical body 3 | 230 mm | 230 mm | 230 mm |
| Distance between lower opening 3B and liquid surface | 20 mm | 20 mm | 20 mm |

TABLE 3-continued

| Liquid amount and liquid depth | 600 ml, 50 mm | 400 ml, 30 mm | 200 ml, 20 mm |
|---|---|---|---|
| Mixing state | Liquid does not rotate vigorously, and is mixed only by its upper portion of about 1 to 2 cm. Mixing state is slightly insufficient. | Liquid rotates, well bubbles, and spatters around. Mixing state is favorable. | Liquid is mixed vigorously and bubbles entirely. Mixing state is extremely favorable. |

According to the foregoing configuration of the air cleaning device 1, the polluted air PA taken in from the air inlets 5, 5, . . . is pressurized by the air blower 4 so as to rotate and descend in a spiral manner, and is blown from the lower opening 3B as an air blowing port toward the liquid surface, and collides with the liquid A and plunges into the container bottom, and then is agitated and mixed with an approximately total amount of the liquid A, as if the air is washed by the liquid. Therefore, the polluted air PA taken in from the air inlets 5, 5, is allowed to contact the liquid A with efficiency.

Accordingly, it is possible to remove pollutants such as dust, dirt, molds, ticks, pollens, and the like, in an efficient manner. In addition, if the liquid A is sterilizing fluid, it is also possible to kill and remove pollutants such as viruses, germs, and the like, in an efficient manner. If the liquid A is deodorant fluid, it is possible to eliminate bad odors of cigarette, formalin, and the like, in an efficient manner. If the liquid A is water, it is possible to remove dust from construction sites, plants, and the like, in an efficient manner.

In addition, the thus configured air cleaning device does not require a pump or a nozzle as described in Patent Document 1 or a pump or a reflector as described in Patent Document 2. Further, differently from the configuration described in Patent Document 3 with rotation of the guide fixed to the rotation shaft of the air blower and extended in the cleaning water, in this configuration, the cylindrical body 3 arranged under the air blower is not driven and the lower opening 3B of the cylindrical body 3 as an air blowing port is separated from the surface of the liquid A, which eliminates the need for a large-capacity air blower or motor and prevents a structure from being complicated. This makes it possible to suppress increase in consumption of energy such as electrical power and manufacturing costs.

In addition, upper and lower metal draining meshes 8 and 9 as liquid removing means are arranged in the middle of a flow path in which the clean air CA having been purified by being agitated and mixed with the liquid A is raised on the outside of the cylindrical body 3 and is discharged from the air outlets 6, 6, . . . . Accordingly, the clean air CA is cleared of the liquid by the liquid removing means before being discharged from the air outlets 6, 6, . . . .

This makes it possible to suppress a content of the liquid in the discharged clean air CA and reduce decrease in amount of the liquid A in the container main body 2, thereby to realize longer time intervals between tasks of refilling the liquid A.

Figure 3:
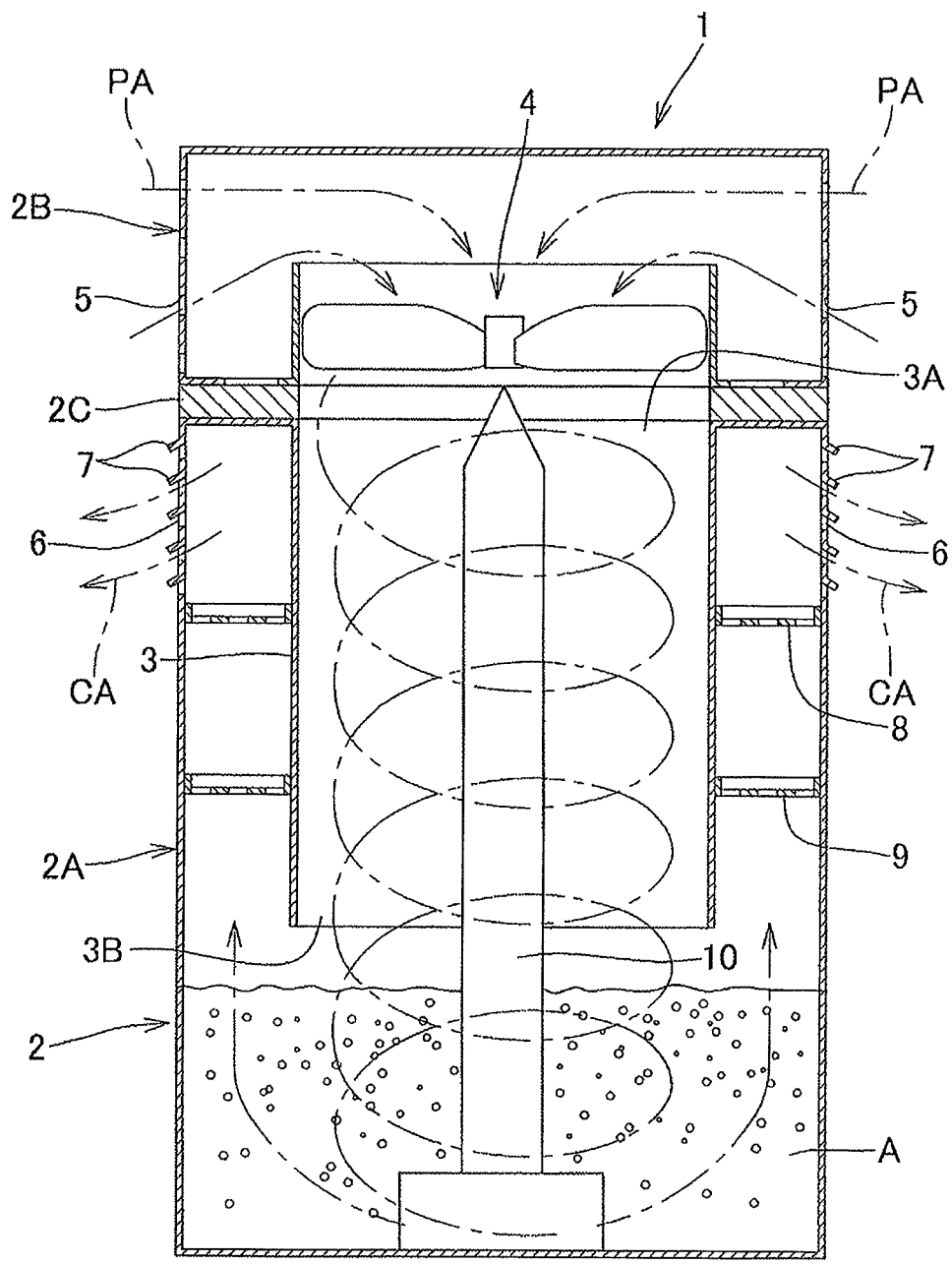

In this arrangement, as shown by a partial longitudinal sectional view of FIG. 3, a bar-like body 10 is provided so as to stand on the bottom of the liquid container 2A as a liquid containing part for containing the liquid A and extend toward an approximate center of the cylindrical body 3, thereby to decrease by the bar-like body 10 a passage section of the polluted air PA blown from the cylindrical body 3 and colliding with the liquid A. Accordingly, the polluted air PA rotating and descending in a spiral manner has an increased pressure to facilitate agitation and mixing of the polluted air PA and the liquid A, which allows the polluted air PA taken in from the air inlets 5, 5, . . . to contact the liquid A with higher efficiency.

Figure 4:
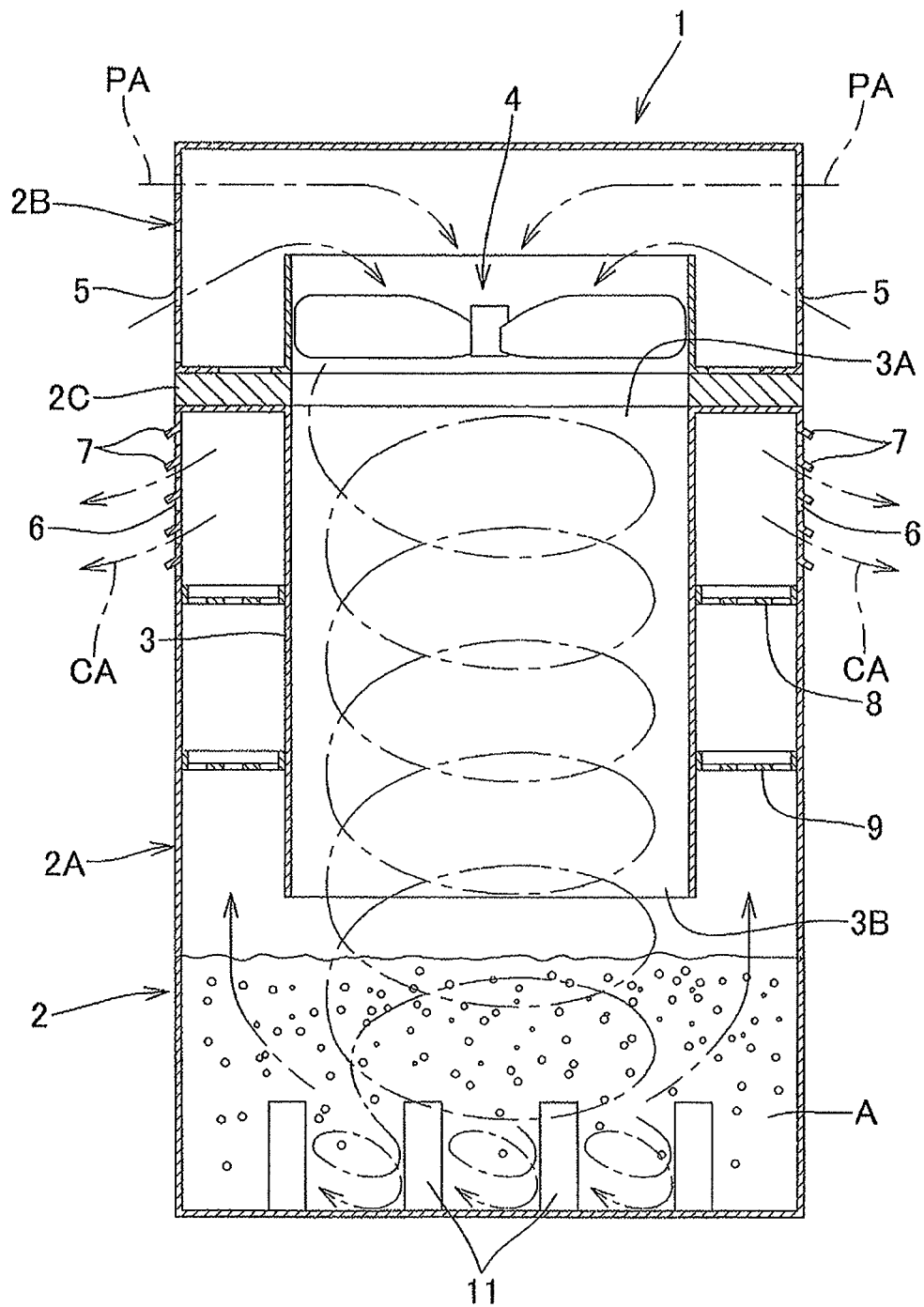

In addition, as shown in the partial longitudinal sectional view of FIG. 4, baffles 11 may be provided so as to project from the bottom of the liquid container 2A. According to this configuration, agitation and mixing of the polluted air PA spirally rotating and descending and the liquid A are facilitated by the agitation facilitating effect of the baffles 11, which allows the polluted air PA taken in from the air inlets 5, 5, . . . to contact the liquid A with higher efficiency.

The baffles 11 may be provided so as to project from portions of the side parts of the liquid container 2A immersed in the liquid A.

Figure 5:
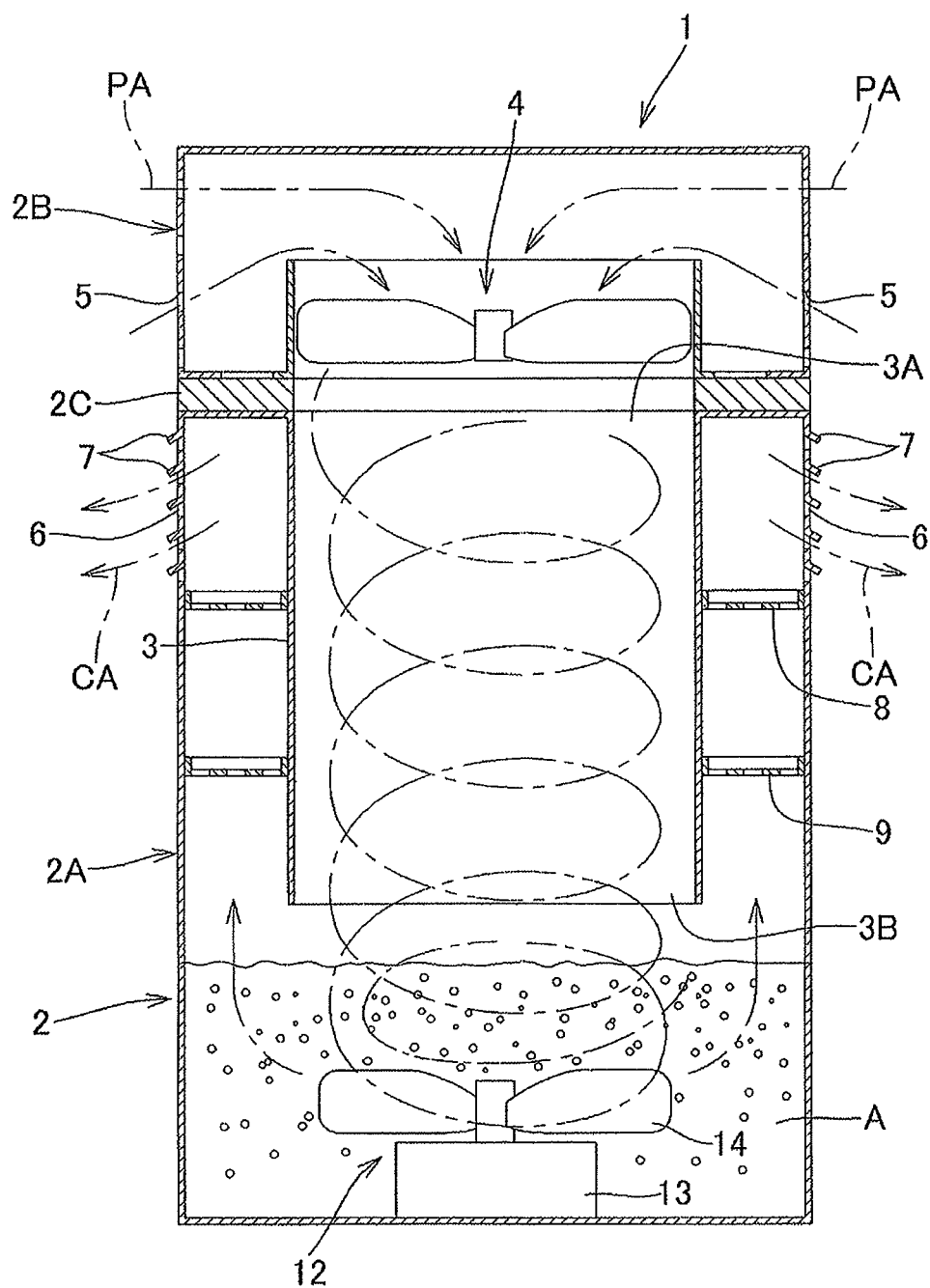

Further, as shown in the partial longitudinal sectional view of FIG. 5, an agitator 12 formed by a motor 13 and agitating blades 14 may be arranged on the bottom of the liquid container 2A. According to this configuration, agitation and mixing of the polluted air PA spirally rotating and descending and the liquid A are facilitated by the agitation facilitating effect of the agitator 12. This allows the polluted air PA taken in from the air inlets 5, 5, . . . to contact the liquid A with higher efficiency.

Figure 6:
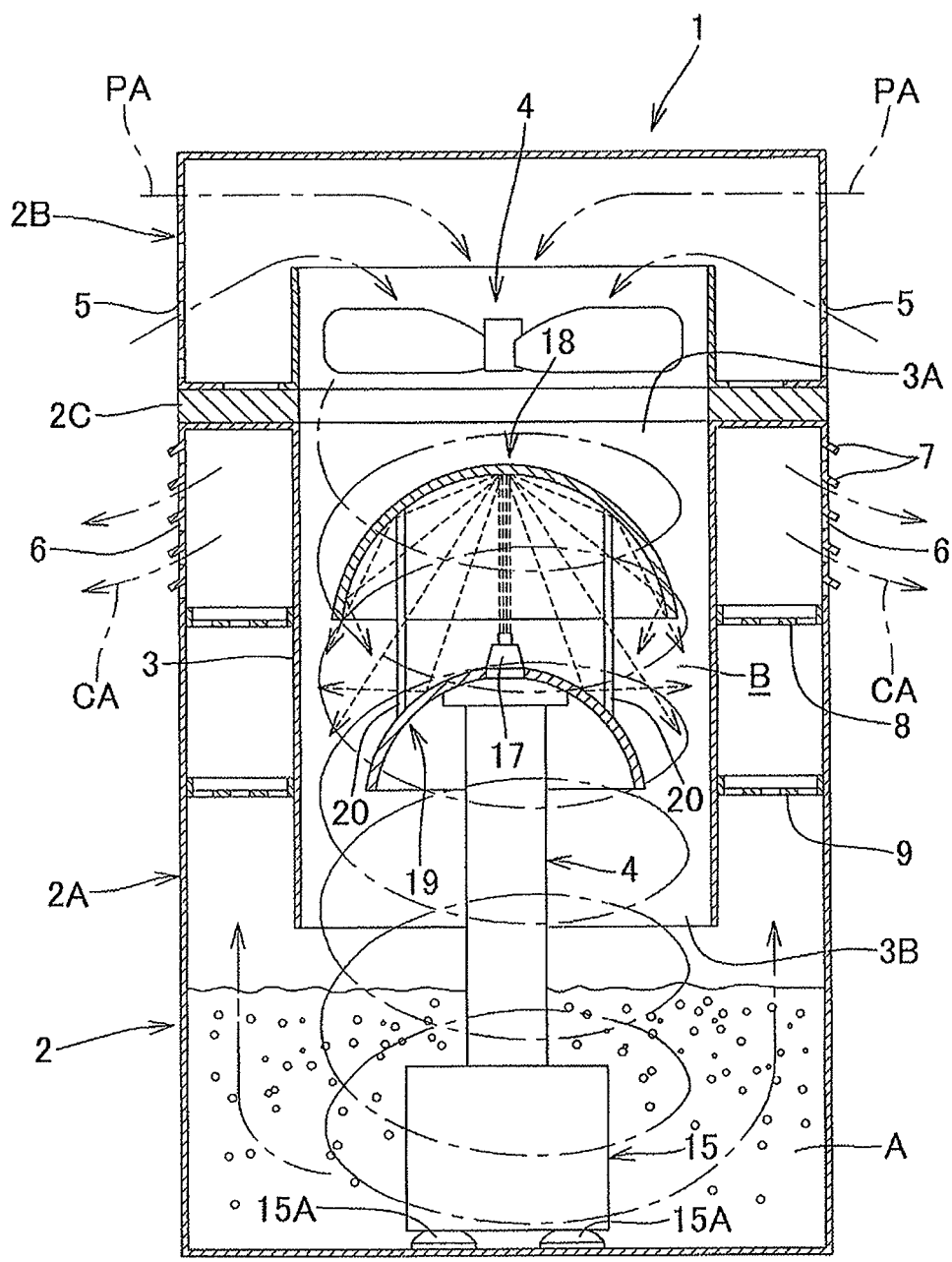

Moreover, as shown in the partial longitudinal sectional view of FIG. 6, the air cleaning device may be configured in such a manner that: the liquid A is pumped up and pressurized, and is ejected upward from a nozzle 17 so as to collide with the reflector 18; the polluted air PA blown from the upper opening 3A into the cylindrical body 3 so as to rotate and descend in a spiral manner, contacts the liquid A colliding with and scattered by the reflector 18, in an internal mixing space B within the cylindrical body 3; a mixture of the polluted air PA falling from the cylindrical body 3 and the scattered liquid A, collides with a puddle of liquid in the container main body 2 and plunges into the bottom of the liquid container 2A such that the polluted air PA is agitated and mixed with the liquid A; and the clean air CA having been agitated and mixed with the liquid A is raised on the outside of the cylindrical body 3 and discharged outside the container main body 2.

Specifically, the air cleaning device 1 shown in FIG. 6 has a pump 15 for pumping up and pressurizing the liquid A sucked and fixed by suction cups 15A, 15A, . . . to the liquid container 2A at a center of an upper surface of the bottom plate. The pump 15 has a discharge opening to which the upwardly directed nozzle 17 is attached directly or via a pipe 16 extending in a vertical direction. Accordingly, the liquid A is ejected as an upward jet flow from the nozzle 17.

In addition, arranged above the nozzle 17 is the bowl-shaped reflector 18 opened downward and separated inward from the cylindrical body 3, which collides with the liquid A ejected upward from the nozzle 17. Arranged under the reflector 18 is a bowl-shaped guide body 19 opened downward and separated inward from the cylindrical body 3, which receives the liquid A colliding with and reflected on the reflector 18, and guides the same outward.

In the configuration of FIG. 6, the guide body 19 is attached to an upper end of the pipe 16 and the reflector 18 is fixed above the guide body 19 using bar-like support members 20, 20, . . . extending in a vertical direction. Alternatively, the reflector 18 may be supported by the cylindrical body 3 using bar-like support members extending in a horizontal direction, for example.

In addition, the reflector 18 and the guide body 19 under the same may not be formed in a bowl-like, downwardly-opened shape, but may be formed in the shape of a hemisphere, a partial hemisphere, a paraboloid, an umbrella, a flat plane, or the like, or may be formed in three dimensions, not two dimensions.

Further, the guide body 19 is not an essential component, and the reflector 18 may be singly provided.

According to the configuration of the air cleaning device 1 shown in FIG. 6, the polluted air PA taken into the container main body 2 is pressurized by the air blower 4, and rotates and descends in a spiral manner by rotation of the blades of the air blower 4 and contact with the inner wall surface of the cylindrical body 3, and the liquid A as a jet flow ejected from the nozzle 17 is scattered by collision with the reflector 18 separated inward from the cylindrical body 3, and the polluted air PA spirally rotating and descending and the liquid A colliding with and scattered by the reflector 18 are brought into contact within the cylindrical body 3, and a mixture of the polluted air PA and the liquid A sharply falls in a bubble state.

The bubbled mixture collides with the liquid A contained in the lower part of the container 2, and penetrates through the puddle of liquid and plunges into the bottom of the liquid containing part 2A (container bottom). Accordingly, the entire liquid puddle is also strongly agitated and mixed in a spiral manner so as to bubble, swell, and increase in volume, as if the polluted air PA is washed by the liquid A. Therefore, the polluted air PA taken into the container main body 2 is allowed to contact the liquid A with extremely high efficiency.

Accordingly, it is possible to remove pollutants such as dust, dirt, molds, ticks, pollens, and the like, in a highly efficient manner. In addition, if the liquid A is sterilizing fluid, it is also possible to kill and remove pollutants such as viruses, germs, and the like, in a highly efficient manner. If the liquid A is deodorant fluid, it is possible to eliminate bad odors of cigarette, formalin, and the like, in a highly efficient manner. If the liquid A is water, it is possible to remove dust from construction sites, plants, and the like, in a highly efficient manner.

Besides, if the polluted air PA taken in from the air inlets 5, 5, . . . is hot wind, for example, the hot wind can be cooled down by airborne droplets of the liquid A colliding with and reflected on the reflector 18 and scattered in various directions. In addition, since the liquid A as a jet flow collides from below with the reflector 18 heated by transfer of forced convection heat from the hot wind, the hot wind can be cooled down via the reflector 18 by high-efficiency colliding jet cooling. Accordingly, in any of cases where the liquid A is sterilizing fluid or deodorant fluid or water, this configuration is suited for cooling hot air in working sites or the like at high temperatures.

Considering these cooling characteristics, the reflector 18 is preferably formed by metal with high thermal conductivity, such as copper or aluminum.

Moreover, differently from the configuration described in Patent Document 3 with rotation of the guide fixed to the rotation shaft of the air blower and extended in the cleaning water, in this configuration, the cylindrical body 3 arranged under the air blower 4 is not driven and the lower opening 3B of the cylindrical body 3 as an air blowing port is separated from the surface of the liquid A, which eliminates the need for a large-capacity air blower or motor and prevents a structure from being complicated. This makes it possible to suppress increase in consumption of energy such as electrical power and manufacturing costs.

Further, when the guide body 19 is provided to receive the liquid A colliding with and reflected from the reflector 18 and guide the same outward, a part of the liquid A scattered by collision with the upper reflector 18, further collides with the lower guide body 19, and is guided outward and scattered by the guide body 19. Accordingly, airborne droplets of the thus scattered liquid A are guided into the mixing space B inside the cylindrical body 3. This increases the density of the airborne droplets of the liquid within the mixing space B, which allows the polluted air PA taken in from the outside to contact the liquid A with higher efficiency.

The air cleaning device 1 described above has one air blower 4 arranged above the cylindrical body 3. Alternatively, a plurality of air blowers may be arranged above the cylindrical body 3. For example, two, three, four, or more air blowers may be arranged in parallel in a horizontal direction (in a horizontal plane).

In addition, the air cleaning device 1 described above includes the container main body 2 that is an approximately circular cylinder in appearance. However, the appearance of the container main body 2 is not limited to an approximately circular cylinder but the container main body 2 may be formed in any other shape such as a polygonal column.

Further, the shapes of the air inlets 5, 5, . . . and the air outlets 6, 6, . . . are not limited to those in this embodiment, but these air inlets and outlets may be provided as round holes, slits, long holes, with any appropriate size.

Moreover, the air inlets may be formed in a top plate as an upper surface of the air blower assembly 2B (container main body 2) or may be used in conjunction with the air inlets 5, 5, . . . in the side surface of the air blower assembly 2B.

In addition, the connecting member 2C may be eliminated between the liquid container 2A and the air blower assembly 2B. The range of vertical division of the container main body 2 and the division structure of the same are not limited to those in this embodiment.

| Reference Signs List | |
|---|---|
| A | Liquid (sterilizing fluid, deodorant fluid, or water) |
| B | Mixing space |
| CA | Clean air |
| PA | Polluted air |
| 1 | Air cleaning device |
| 2 | Container main body |
| 2A | Liquid container (liquid containing part) |
| 2B | Air blower assembly |
| 2C | Connecting member |
| 3 | Cylindrical body |
| 3A | Upper opening (air blowing port) |
| 3B | Lower opening (air discharging port) |
| 4 | Air blower |
| 5 | Air inlet |
| 6 | Air outlet |
| 7 | Louver |
| 8, 9 | Metal mesh (liquid removing means) |
| 10 | Bar-like body |
| 11 | Baffle |
| 12 | Agitator |
| 13 | Motor |
| 14 | Agitating blade |
| 15 | Pump |
| 15A | Suction cup |
| 16 | Pipe |
| 17 | Nozzle |

-continued

Reference Signs List

| 18 | Reflector |
| 19 | Guide body |
| 20 | Support member |
| 21 | Power cord |
| 22 | Power plug |
| 23 | Switch |

The invention claimed is:

1. An air cleaning method, comprising:
pressurizing by an air blower air taken into a container main body containing a liquid as sterilizing fluid, deodorant fluid, or water;
blowing the air pressurized by the air blower into a cylindrical body, spaced from the container main body, which has upper and lower openings and extends in a vertical direction, from the upper opening, the lower opening being an air blowing port separated from a surface of the liquid;
blowing out of the lower opening, the air blown from the upper opening into the cylindrical body and rotating and descending in a spiral manner, so as to collide with the liquid, plunging the air into a bottom of a liquid containing part for containing the liquid in the container main body, and agitating and mixing the air and the liquid; and
raising the air agitated and mixed with the liquid on an outside of the cylindrical body, and discharging the same through an outlet in a side wall of the container main body to an outside of the container main body.

2. An air cleaning method, comprising:
pressurizing by an air blower air taken into a container main body containing a liquid A as sterilizing fluid, deodorant fluid, or water;
blowing the air pressurized by the air blower into a cylindrical body, spaced from the container main body, which has upper and lower openings and extends in a vertical direction, from the upper opening, the lower opening being an air blowing port separated from a surface of the liquid;
pumping up and pressurizing the liquid, and ejecting the liquid upward from the nozzle so as to collide with a reflector separated inward from the cylindrical body;
contacting the air blown from the upper opening into the cylindrical body and rotating and descending in a spiral manner with the liquid colliding with and scattered by the reflector;
causing a mixture of the air falling from the cylindrical body and the scattered liquid to collide with a puddle of liquid in the container main body, plunging the mixture into a bottom of a liquid containing part for containing the liquid in the container main body, and agitating and mixing the air with the liquid; and
raising the air agitated and mixed with the liquid on an outside of the cylindrical body and discharging the same through an outlet in a side wall of the container main body to an outside of the container main body.

3. The air cleaning method according to claim 1 or 2, wherein the air agitated and mixed with the liquid is raised on the outside of the cylindrical body and the liquid is removed from the air in the middle of a flow path for discharging the air to the outside of the container main body.

4. An air cleaning device, comprising:
a container main body which contains a liquid as sterilizing fluid, deodorant fluid, or water;
a cylindrical body, spaced from the container main body, having upper and lower openings and extending in a vertical direction, which is arranged within the container main body such that the lower opening is separated from a surface of the liquid;
an air blower which is arranged above the cylindrical body within the container main body, and pressurizes the air taken in from an air inlet of the container main body, and blows the same from the upper opening as an air blowing port into the cylindrical body; and
an air outlet which is formed on an outside of the cylindrical body of the container main body, wherein
the air blown by the air blower from the upper opening into the cylindrical body, rotates and descends in a spiral manner and is blown out from the lower opening as an air blowing port, and collides with the liquid and plunges into a bottom of a liquid containing part for containing the liquid in the container main body, and is agitated and mixed with the liquid, and
the air agitated and mixed with the liquid is raised on the outside of the cylindrical body and is discharged from the air outlet.

5. The air cleaning device according to claim 4, wherein a body shaped as a bar is provided so as to stand on the bottom of the liquid containing part and extend toward an approximate center of the cylindrical body.

6. The air cleaning device according to claim 4, wherein a baffle is provided so as to project from the bottom or side of the liquid containing part.

7. The air cleaning device according to claim 4, wherein an agitator is arranged on the bottom of the liquid containing part.

8. An air cleaning device, comprising:
a container main body which contains a liquid as sterilizing fluid, deodorant fluid, or water;
a cylindrical body, spaced from the container main body, having upper and lower openings and extending in a vertical direction, which is arranged within the container main body such that the lower opening is separated from a surface of the liquid;
an air blower which is arranged above the cylindrical body within the container main body, and pressurizes the air taken in from an air inlet of the container main body, and blows the same from the upper opening as an air blowing port into the cylindrical body;
a pump which pumps up and pressurizes the liquid;
a nozzle which is upwardly attached to a discharging port of the pump;
a reflector which is provided above the nozzle, and is separated inward from the cylindrical body, and collides with the liquid as a jet flow ejected from the nozzle and reflects the same; and
an air outlet which is formed on an outside of the cylindrical body of the container main body,
wherein the air blown by the air blower from the upper opening into the cylindrical body, rotates and descends in a spiral manner, and contacts the liquid colliding with and scattered by the reflector, and a mixture of the air falling from the lower opening as an air blowing port and the scattered liquid collides with a puddle of liquid in the container main body and plunges into a bottom of a liquid containing part for containing the liquid in the container main body, and is agitated and mixed with the liquid, and
the air agitated and mixed with the liquid is raised on the outside of the cylindrical body and is discharged from the air outlet.

9. The air cleaning device according to claim 8, wherein a guide body is provided within the cylindrical body under the reflector so as to receive the liquid colliding with and reflecting on the reflector, and guide the same outward.

10. The air cleaning device as in any one of claims 4 to 9, wherein liquid removing means are provided in the middle of a flow path for raising the air agitated and mixed with the liquid on the outside of the cylindrical body and discharging the same from the air outlet.

* * * * *